United States Patent [19]

Knifton

[11] Patent Number: 5,099,072
[45] Date of Patent: Mar. 24, 1992

[54] METHOD FOR ONE-STEP SYNTHESIS OF METHYL T-BUTYL ETHER

[75] Inventor: John F. Knifton, Austin, Tex.

[73] Assignee: Texaco Chemical Company, White Plains, N.Y.

[21] Appl. No.: 494,280

[22] Filed: Mar. 16, 1990

Related U.S. Application Data

[63] Continuation-in-part of Ser. No. 168,063, Mar. 14, 1988, abandoned.

[51] Int. Cl.$^5$ .............................................. C07C 41/09
[52] U.S. Cl. .................................................... 568/698
[58] Field of Search ......................................... 568/698

[56] References Cited

U.S. PATENT DOCUMENTS

| | | | |
|---|---|---|---|
| 2,282,469 | 5/1942 | Frolich | 568/698 |
| 4,058,576 | 11/1977 | Chang et al. | |
| 4,590,294 | 5/1986 | Ballantine et al. | 568/698 |
| 4,918,244 | 4/1990 | Nelson et al. | 568/698 |

OTHER PUBLICATIONS

Adams et al., Clays & Clay Minerals, vol. 34, No. 5, 597-603, 1986.
Figueras, Catal. Rev. -Sci. Eng. 30(3) 457-499, 1988.

*Primary Examiner*—Howard T. Mars
*Attorney, Agent, or Firm*—Jack H. Park; Kenneth R. Priem; Cynthia L. Kendrick

[57] ABSTRACT

A method is disclosed wherein t-butanol is reacted with methanol in a reaction zone in the presence of a catalyst to provide methyl-tert-butyl ether and the improvement of accomplishing the reaction in one-step which comprises:

a. using an acidic montmorillonite silica-alumina catalyst;
b. continuously contacting said t-butanol and methanol in a molar amount of about 0.1 to 10 moles of methanol per mole of t-butanol with said catalyst at a temperature of about 20° C. to about 250° C. and a pressure of about atmospheric to about 1000 psig to obtain the methyl-tert-butyl product.

1 Claim, No Drawings

METHOD FOR ONE-STEP SYNTHESIS OF METHYL T-BUTYL ETHER

CROSS-REFERENCE

This application is a continuation-in-part of U.S. Ser. No. 07/168,063, to be abandoned and is related to Ser. No. 07/494,281.

This invention concerns an improved process for preparing methyl tertiary butyl ether by the reaction of tertiary butanol and methanol in the presence of a catalyst containing acidic clay or clay mineral catalysts containing alumina and silica, such as smectite clays, including acidic montmorillonite silica-alumina clays. The invention is particularly advantageous in that the reaction takes place in one-step, the catalyst exhibits excellent selectivity to the desired ether product and high levels of tert-butanol conversion are achieved.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether (MTBE) are based upon the liquid-phase reaction of isobutylene and methanol (eq. 1), catalyzed by a cationic ion-exchange resin (see, for example: Hydrocarbon Processing, Oct. 1984, p. 63; Oil and Gas J., Jan. 1, 1979, p. 76; Chem. Economics Handbook-SRI, Sept. 1986, p. 543-7051P). The cationic ion-exchange resins used in MTBE synthesis normally have the sulphonic acid functionality (see: J. Tejero, J. Mol. Catal., 42 (1987) 257; C. Subramamam et al., Can. J. Chem. Eng., 65 (1987) 613).

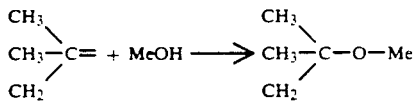

(Eq. 1)

With the expanding use of MTBE as an acceptable gasoline additive, however, a growing problem is the availability of raw materials. Historically, the critical raw material is isobutylene (Oil and Gas J., June 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (TBA) is readily available commercially through isobutane oxidation.

In U.S. Pat. No. 4,144,138 (1979) to Rao et al., there is disclosed a method for recovering methyl tertiary butyl ether from etherification reaction effluent by azeotropic distillation to recover methanol-ether azeotrope overhead which is water-washed to give pure ether raffinate, the latter being azeotropically distilled to yield ether-methanol overhead which is recycled to water washing.

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl. Vses Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process. It is also pointed out that, although a plant for etherification over cation exchangers does not present any problems, considerations include the fact that recycling large amounts of tert-butyl alcohol and methanol, as well as isobutylene, causes the scheme to be somewhat more expensive. Also, the progress of the reaction over cation exchangers is usually complicated by various adsorption and diffusion factors, by swelling phenomena, and by the variable distribution of the components between the solution and ion-exchanger phase. Furthermore, said acidic cation-exchangers with an organic (polystyrene or polymethacrylate) backbone generally have a very limited stability range with regard to operating temperatures, with temperatures above 120° C. normally leading to irreversible destruction of the resin and loss of catalytic activity.

In an article titled "Catalysis: Selective Developments", Chem. Systems Report 84-3, 239-249, at section 3.4320, the unusual properties of smectite clays which make them of interest as catalysts are discussed. These compositions are layered and exhibit a 2:1 relationship between tetrahedral and octahedral sites. In addition the combination of cation exchange, intercalation and the fact that the distance between the layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

G. B. Patent No. 2,179,563 (1987) discloses the use of modified layered clay catalysts in reactions capable of catalysis by protons. Of particular interest in this invention were the three-layer sheet types, such as smectites, micas and vermiculites composed of successive layers of tetrahedral silica, octahedral alumina and tetrahedral silica which can exhibit swelling properties.

U.S. Pat. No. 4,590,294 discloses a process for the production of an ester comprising reacting an olefin from the group consisting of ethylene, hex-1-ene, hept-1-ene, oct-1-ene, 4-methylpent-1-ene, hex-2-ene, 1,5-hexadiene and cyclohexene with a carboxylic acid using as a catalyst component a hydrogen ion-exchanged layered clay. This reference would not seem to suggest a method for simultaneous dehydration of tert-butanol to iso-butylene and the reaction with methanol to produce MTBE.

It would be a substantial advance in the art if methyl tertiary butyl ether could be selectively synthesized from tertiary butyl alcohol and methanol in one step using a clay mineral catalyst which allows for rapid conversion of t-butanol.

SUMMARY OF THE INVENTION

In accordance with certain of its aspects, the novel method of this invention for preparing methyl tert-butyl ether from tertiary butyl alcohol (t-butanol) and methanol in one-step comprises reacting tertiary butyl alcohol and methanol in the presence of a catalyst comprising acidic montmorillonite silica-alumina clays.

DESCRIPTION OF THE INVENTION

Preparation of the product of this invention may be carried out typically by reacting tertiary butyl alcohol and methanol in the presence of an etherification catalyst. The etherification is carried out in one step and the catalyst preferably comprises an acidic montmorillonite silica-alumina clay catalyst.

The reaction can be represented by the following:

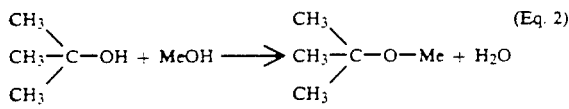

Generally the methanol and t-butanol coreactants may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

The same process may also be applied to the preparation of other alkyl tertiary alkyl ethers. For example, said process may be applied to the reaction of a $C_1$-$C_6$ primary alcohol such as methanol, ethanol, n-propanol and n-hexanol with a $C_4$-$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols. e.g., a mixture of $C_1$-$C_5$ alcohols, could be reacted to give a mixture of alkyl tert-alkyl ethers.

The catalysts used to effect this reaction are silica-alumina clays. Chemically, clays are composed primarily of silicon, aluminum and oxygen, with minor amounts of magnesium and iron in some cases. Variations in the ratios of these constituents, and their crystal lattice configurations, results in some fifty separate clays, each with its own characteristic properties.

Particularly effective in reaction (Eq. 2) are smectite clays. Smectite clays are discussed in the article cited in Chem. Systems Report, 84-3. These clays have small particle size and unusual intercalation properties which afford them high surface area. They are alumino silicates with a unique structure that permits modifications which should provide useful catalysts. They comprise layered sheets of octahedral sites between sheets of tetrahedral sites, where the distance between the layers can be adjusted by swelling. This layering is illustrated in an article by F. Figueras, Catal. Rev.-Sci. Eng., 30, 457 (1988). What renders the smectites of interest among the clay minerals is the combination of cation exchange, intercalation, and the fact that the distance between the layers can be adjusted by treatment with the appropriate solvent etc.

The three layered sheet types include montmorillonite, vermiculite and some brittle mica. The idealized basic structure of clays of this type is that of a pyrophyllite which has the basic formula $Si_8Al_4O_{20}(OH)_4$.

A general representation of the montmorillonite structure is:

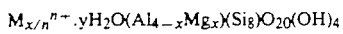

Where: M represents the interlamellar (balancing cations), normally sodium or lithium. x, y and n are integers.

Said montmorillonite clays are best used in the present application in an acidic form. Mineral acids such as sulfuric acid and phosphoric acid activate montmorillonites by attacking and solubilizing structural cations in the octahedral layers. This opens up the clay structure and increases surface area. These acid treated clays act as strong Bronsted acids.

Acidic montmorillonite clays are the preferred form of mineral clay in the present invention. Said clays should preferably have a residual acidity in the range 0.1 to 30 mg KOH/gm (titrated to phenolphthalein end point), a surface area of 10 to 1000 $m^2$/gm, and a moisture content of up to 20 wt %. Illustrative examples include Engelhard Powdered Clay-113, having a residual acidity of 10 mg KOH/gm, surface area of 300 $m^2$/gm and a moisture content of 4 wt %, Clay-13, having an acidity of 16 mg KOH/gm, a surface area of 300 $m^2$/gm and a moisture content of 16 wt %, granular Clay-24, of particle size 20/60 mesh, having an acidity of 16 mg KOH/gm, a surface area of 300 $m^2$/gm and a moisture content of 10 wt %, granular Clay-25, of particle size 10/20 mesh, having an acidity of 16 mg KOH/gm, a surface area of 400 $m^2$/gm and a moisture content of 12 wt %, granular Clay-224, of particle size 20/60 mesh, having an acidity of 3.0 mg KOH/gm, a surface area of 350 $m^2$/gm and a moisture content of <1 wt %, as well as extruded Clay-62, which may, for example, be in 1/16" or 3/16" diameter extrudates, and have acidity of ca. 3.0 mg KOH/gm, a surface area of 275 $m^2$/gm and a moisture content of less than 1%.

Most preferred are montmorillonite clays with a residual titratable acidity in the range of 1 to 20 mg KOH, a surface area of 100 to 500 $m^2$/gm and a moisture content of <1%. Illustrative of such clays is Engelhard's Grade-224 clay granules. Such clays are most effective where MTBE is being generated at high (>70%) t-butanol conversion levels using tBA:MeOH molar ratios close to unity (i.e. in the range 1:1→1.2:1). In these cases, the total MTBE+isobutylene yields (basis tBA converted) will be near quantitative (100 mole %). This condition is illustrated by the accompanying Example VII. Such crude product mixtures, comprising MTBE, isobutylene, water and unreacted methanol plus t-butanol, may, under certain circumstances, comprise two phases where the tBA conversion levels are high (i.e. >80%). These two phases would generally be composed of an isobutylene/MTBE-rich phase, and an aqueous methanol-rich phase. Such a separation is particularly advantageous in allowing the MTBE product to be easily isolated from the crude product mix, while the isobutylene by-product could be fed to a second etherification unit (with added methanol) in order to generate additional MTBE.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. The total operating pressure may be from 0 to 1000 psig, or higher. The preferred pressure range is 50 to 500 psig.

Typically, MTBE is generated continuously in up to ca. 45 wt % concentration in the crude liquid product at total liquid hourly space velocities (LHSV) of up to 8 and relatively mild conditions, where:

$$LHSV = \frac{\text{Volume Of Total Liquid Feed Run Through The Reactor Per Hour}}{\text{Volume of Catalyst In Reactor}}$$

The examples which follow illustrate the one-step synthesis of MTBE from TBA and MeOH (Eq. 2) using acidic montmorillonite silica-alumina catalysts, particularly those of high acidity in the form of high surface area extrudates and powders.

Said catalysts can be in the form of powders, pellets, granules, spheres, shapes and extrudates. The examples described herein demonstrate the advantages of using granules and powders. The examples are only intended as a means of illustration and it is understood the invention is not meant to be limited thereby.

Conversions of t-butanol (TBA, wt %) are estimated in the following examples using the equation:

$$\frac{(\text{Wt \% Conc. of TBA in Feed} - \text{Wt \% Conc. of TBA in Product})}{\text{Wt \% Conc. of TBA in Feed}} \times 100$$

Yields of methyl t-butyl ether (MTBE, mole %) are estimated from:

$$\frac{\text{Moles of MTBE in Product Liquid}}{\text{moles of TBA converted}} \times 100$$

Examples I through VI illustrate the one-step synthesis of MTBE from TBA and MeOH using acidic clay catalysts, particularly montmorillonite acidic clays.

EXAMPLE I

The synthesis was conducted in a tubular reactor (0.563" i.d.; 12" long), constructed of 316 stainless steel, operated upflow and mounted in a furnace, controllable to or $-1.0°$ C. and fitted with pumps allowing flow control to $< +$ or $-1$ cc/hr. The reactor was also fitted with a pressure regulating device and equipment for monitoring temperature, pressure and flow rate.

The reactor was charged at the beginning of the experiment with 25 cc of Engelhard Filtrol Grade-113 powder, having a residual acidity of 10 mg KOH/gm, surface area of 300 $m^2$/gm and moisture content of 4 wt %. A screen of experiment with 25 cc of Engelhard Filtrol Clay-113. A screen of glass beads was placed at the top and bottom of the reactor to ensure the clay powder would remain in the middle portion.

The catalyst bed was first conditioned overnight by washing with methanol/t-butanol (2:1 molar mix) at 120° C., 300 psi back pressure and a liquid flow rate of 25 cc/hr. The same solution of methanol (1281.6 g, 40 moles) plus t-butanol (1482.4 g 20 moles) was then pumped through the catalyst bed at 25 cc/hr, while the reactor was held at 120° C. at a total pressure of 300 psi. Samples of the product were taken periodically, either by trapping in a dry ice cooled container, or by collecting on-stream (on-line) in a 316 stainless steel bomb. Typical analyses data for samples taken under those conditions are summarized in Table I.

Catalyst performance at higher temperatures and liquid flow rates were also measured, after reaching equilibrium conditions overnight. Summary data for these three runs are also given in Table I.

It should be noted that with this catalyst, MTBE is generated in ca. 40% concentration when run at LHSV of 8 (e.g. Sample #21). The operating conditions are moderate (150° C., 300 psi) and for Sample #21:
Estimated TBA conversion per pass = 78%
MTBE yield (basis TBA converted) = 81 mole %

EXAMPLES II TO VI

Using the procedures and analyses methods of Example I, these examples illustrate the synthesis of MTBE from methanol plus t-butanol mix (2:1 molar mix) employing other acidic clay catalysts over a range of operating conditions. Of note:

a) A sample of Engelhard Filtrol Grade-13 powder, having an acidity of 15 mg KOH/gm, surface area 300 $m^2$/gm and a moisture content of 16 wt %, also gave MTBE in 38% concentration when run at 150° C. and LHSV of 8 (see Table I, Sample #18).

b) Clay-13, when operated at 150° C., 300 psi, with LHSV of 8, will maintain activity over at least 300 hours (see Table II).

c) A granular form of acidic clay Engelhard Filtrol Grade-24, having an acidity of 16 mg KOH/gm, surface area of 300 $m^2$/gm, a moisture content of 10 wt % and a particle size of 20/60 mesh, is effective as a MTBE catalyst over the temperature range 80° to 150° C. and LHSV's of 1 to ca. 7 (see Table III). In this experiment:

i) At 120° C., Example IV, Sample #6:
  MTBE Concentration In Product Is 44 wt %
  tBA Conversion = 77%
  MTBE Yield = 91 mole % ii) At 100° C., on the other hand, Example V, Sample #6 shows:
  MTBE Concentration In Product Is 44 wt %
  tBA Conversion = 74%
  MTBE Yield = 94 mole % iii) Finally, at 80° C., Example V, Sample #20, shows:
  tBA Conversion = 32%
  MTBE Yield = 91 mole % d) By contrast, an extruded form of acidic clay, Engelhard Filtrol Grade-62, 3/16" diameter extrudates, having an acidity of 3.0 mg KOH/g, surface area of 275 $m^2$/gm and a moisture content of <1%, proved to be less effective in MTBE service in terms of both MTBE concentration and yield in the product effluent (see Table IV, and compare with data in Table IV). At 150° C.,
Example VI, Sample #7 shows:
MTBE Concentration In Product Liquid of 34 wt %
tBA Conversion = 71%
MTBE Yield = 75 mole %

EXAMPLE VII

Using the procedures and analyses methods of Example I, this example illustrates the synthesis of methyl t-butyl ether from methanol plus t-butanol where the MeOH-to-t-BuOH molar feed ratio is 1.1:1 and the catalyst is Engelhard Grade-224 granules having an acidity of 3.0 mg KOH/g, a surface area of 350 $m^2$/gm and a moisture content of <1 wt %. A range of operating conditions have been considered, including changes in operating temperature and feed rate. The results are summarized in Table V. Of note:

At 140° C., Example VIIB, Sample #1 shows:

MTBE Concentration In The Crude Liquid Product Of 38.1%
tBA Conversion = 71%
MTBE Yield = 65.1 mole %
MTBE + Isobutylene Yield = 99.9 mole %

At 180° C., Example VIIA, Sample #5 is two layers, an isobutylene/MTBE rich phase and a heavier aqueous methanol phase. Estimated tBA conversion in this case is ca. 88%.

At 160° C. and a LHSV = 5, Example VIIB, Sample #5 exhibits good (75%) t-butanol conversion levels and high concentrations of MTBE in the product effluent. At 160° C. and LHSV = 2, the t-butanol conversion level is 83% (Sample #3).

TABLE I

| Example | Catalyst | Feed Sample | Flow Rate (cc/hr) | Pressure (psig) | Temp. (°C.) | Sample | MTBE | i-C$_4$ | MeOH | tBA | H$_2$O |
|---|---|---|---|---|---|---|---|---|---|---|---|
| | | F | | | | | | | | 45.5 | 54.2 |
| I | Clay-113[a] | | 25 | 300 | 120 | #3 | 28.4 | 1.9 | 35.3 | 25.7 | 8.6 |
| | | | | | | #5 | 29.6 | 2.2 | 35.4 | 25.2 | 7.6 |
| | | | | | | #6 | 27.5 | 2.3 | 36.5 | 27.5 | 6.2[b] |
| | | | 25 | 300 | 150 | #8 | 37.6 | 9.4 | 30.9 | 11.2 | 10.0 |
| | | | | | | #9 | 38.1 | 5.0 | 32.5 | 11.9 | 11.5 |
| | | | | | | #10 | 38.5 | 3.7 | 33.1 | 12.2 | 11.7 |
| | | | 100 | 300 | 150 | #14 | 36.4 | 4.1 | 33.0 | 16.1 | 10.3 |
| | | | | | | #15 | 36.7 | 5.3 | 32.4 | 15.5 | 10.0 |
| | | | | | | #16 | 37.0 | 5.2 | 32.4 | 15.3 | 10.0 |
| | | F-1 | | | | | | | | 46.2 | 53.7 |
| | | | 200 | 300 | 150 | #18 | 39.9 | 6.2 | 31.9 | 12.1 | 9.9 |
| | | | | | | #19 | 40.0 | 6.2 | 31.9 | 12.1 | 9.8 |
| | | | | | | #21 | 40.0 | 6.0 | 31.8 | 12.1 | 9.9 |
| | | F | | | | | | | | 46.3 | 53.6 |
| II | Clay-13[c] | | 25 | 300 | 120 | #2 | 29.4 | 2.2 | 36.1 | 25.2 | 7.0 |
| | | | | | | #3 | 29.3 | 2.3 | 36.0 | 25.3 | 7.0 |
| | | | | | | #6 | 31.9 | 3.2 | 34.5 | 24.6 | 5.8[b] |
| | | | 25 | 300 | 150 | #7 | 37.4 | 9.8 | 31.3 | 10.3 | 9.7 |
| | | | | | | #11 | 37.7 | 5.4 | 33.6 | 11.2 | 10.7 |
| | | | | | | #12 | 36.6 | 6.9 | 33.4 | 11.8 | 9.9[b] |
| | | | 200 | 300 | 150 | #13 | 37.9 | 6.9 | 32.8 | 12.2 | 10.0 |
| | | | | | | #14 | 37.8 | 6.3 | 33.2 | 12.9 | 9.8 |
| | | | | | | #18 | 38.0 | 8.0 | 32.5 | 12.3 | 9.2[b] |

[a] Engelhard, Clay-113
[b] On-Line Sample
[c] Engelhard, Clay-13

TABLE II

| Example | Catalyst | Sample | MTBE | i-C$_4$ | MeOH | TBA | H$_2$O | Stream (Days) |
|---|---|---|---|---|---|---|---|---|
| III | Clay-13[a] | #1 | 39.3 | 5.6 | 32.8 | 11.7 | 10.3 | 1 |
| | | #2 | 39.2 | 6.7 | 32.5 | 11.3 | 10.1 | 2 |
| | | #3 | 39.6 | 6.2 | 32.6 | 11.5 | 10.0 | 3 |
| | | #4 | 39.5 | 6.0 | 32.9 | 11.6 | 9.9 | 4 |
| | | #5 | 38.9 | 5.9 | 33.2 | 12.0 | 9.9 | 5 |
| | | #6 | 39.7 | 2.5 | 34.6 | 12.2 | 10.9 | 7 |
| | | #7 | 39.3 | 6.1 | 33.4 | 11.1 | 10.1 | 8 |
| | | #8 | 38.2 | 6.6 | 32.9 | 12.5 | 9.6 | 9 |
| | | #9 | 38.0 | 6.2 | 33.2 | 13.0 | 9.6 | 10 |
| | | #10 | 37.9 | 6.4 | 33.2 | 12.8 | 9.6 | 11 |
| | | #11 | 38.1 | 2.0 | 35.7 | 13.3 | 10.9 | 14 |
| | | #12 | 35.7 | 5.2 | 34.4 | 15.4 | 9.1 | 14 |
| | | #13 | 33.9 | 6.0 | 34.5 | 16.8 | 8.6 | 15 |

[a] Run at 200 cc/hr, 150° C., 300 psi

TABLE III

| Example | Catalyst | Feed Sample | Flow Rate (cc/hr) | Pressure (psig) | Temp. (°C.) | Sample | MTBE | i-C$_4$ | MeOH | tBA | H$_2$O |
|---|---|---|---|---|---|---|---|---|---|---|---|
| | | F | | | | | | | | 46.4 | 53.5 |
| IV | Clay-24[a] | | 25 | 300 | 120 | #2 | 45.3 | 3.7 | 30.0 | 11.7 | 9.2 |
| | | | | | | #5 | 43.6 | 3.1 | 31.1 | 12.4 | 9.7 |
| | | | | | | #6 | 44.4 | 3.8 | 30.6 | 12.4 | 8.8[b] |
| | | | 25 | 300 | 150 | #8 | 36.8 | 6.0 | 33.7 | 10.8 | 10.7 |
| | | | | | | #10 | 37.1 | 4.2 | 34.4 | 11.1 | 11.1 |
| | | | | | | #12 | 36.3 | 7.5 | 33.5 | 10.6 | 9.9[b] |
| | | | 120 | 300 | 150 | #13 | 38.6 | 6.2 | 33.4 | 11.1 | 10.2 |
| | | | | | | #17 | 38.3 | 7.0 | 33.2 | 10.9 | 10.1 |
| | | | | | | #18 | 38.1 | 8.2 | 32.7 | 10.8 | 9.6[b] |
| | | F | | | | | | | | 46.3 | 53.6 |
| V | Clay-24[a] | | 25 | 300 | 100 | #1 | 44.2 | 2.8 | 30.3 | 13.7 | 9.0 |
| | | | | | | #5 | 43.9 | 1.8 | 30.9 | 14.2 | 9.2 |
| | | | | | | #6 | 44.0 | 2.6 | 30.8 | 14.1 | 8.5[b] |
| | | | 120 | 300 | 100 | #7 | 30.1 | 2.3 | 35.8 | 25.4 | 6.4 |

TABLE III-continued

| Example | Catalyst | Feed Sample | Flow Rate (cc/hr) | Pressure (psig) | Temp. (°C.) | Sample | MTBE | i-C$_4$ | MeOH | tBA | H$_2$O |
|---|---|---|---|---|---|---|---|---|---|---|---|
| | | | 25 | 300 | 80 | #11 | 30.0 | 2.1 | 36.0 | 25.7 | 6.3 |
| | | | | | | #12 | 29.7 | 2.7 | 35.9 | 25.6 | 6.1[b] |
| | | | | | | #15 | 18.0 | 1.6 | 40.3 | 36.6 | 3.5 |
| | | | | | | #19 | 17.9 | 1.3 | 40.3 | 36.9 | 3.5 |
| | | | | | | #20 | 18.2 | 1.4 | 40.2 | 36.6 | 3.6[b] |

[a]Engelhard, Clay-24
[b]On-Line Sample

TABLE IV

| Example | Catalyst | Feed Sample | Flow Rate (cc/hr) | Pressure (psig) | Temp. (°C.) | Sample | MTBE | i-C$_4$ | MeOH | tBA | H$_2$O |
|---|---|---|---|---|---|---|---|---|---|---|---|
| VI | Clay-62[a] | F1 | | | | | | | 46.5 | 53.4 | |
| | | | 25 | 300 | 120 | #1 | 15.8 | 3.3 | 40.8 | 36.4 | 3.7 |
| | | | | | | #5 | 15.4 | 2.1 | 41.3 | 37.7 | 3.5 |
| | | | | | | #6 | 15.4 | 2.6 | 41.3 | 37.5 | 3.2 |
| | | | 25 | 300 | 150 | #7 | 33.7 | 8.7 | 33.7 | 15.6 | 8.2 |
| | | | | | | #11 | 33.3 | 5.6 | 35.4 | 16.7 | 8.8 |
| | | | | | | #12 | 32.1 | 7.5 | 35.4 | 17.3 | 7.8 |
| | | | 150 | 300 | 150 | #14 | 15.1 | 4.6 | 40.7 | 35.8 | 3.8 |
| | | | | | | #16 | 14.0 | 3.1 | 41.7 | 37.8 | 3.4 |
| | | | | | | #18 | 14.7 | 3.8 | 41.4 | 36.7 | 3.4 |

[a]Engelhard, Clay-62

TABLE V

| Example | Catalyst | MeOH/tBA Molar Ratio | Temp. (°C.) | Flow Rate (cc/hr) | Sample | H$_2$O | MeOH | i-C$_4$ | tBA | MTBE |
|---|---|---|---|---|---|---|---|---|---|---|
| VIIA | Clay-224[a] | 1.1:1 | | | F-A | | 30.2 | 69.5 | | |
| | | | 100 | 50 | #1 | 4.6 | 24.2 | 4.0 | 47.1 | 20.0 |
| | | | | | #2 | 3.0 | 24.0 | 3.2 | 47.0 | 21.4 |
| | | | 120 | 50 | #3 | 7.7 | 22.1 | 7.2 | 34.6 | 28.3 |
| | | | | | #4 | 6.9 | 21.5 | 7.6 | 36.3 | 27.6 |
| | | | 180 | 50 | #5 | 4.9 | 19.5 | 27.6 | 8.8 | 38.5 |
| | | | | | | 28.2 | 43.0 | 8.2 | 8.3 | 11.6 |
| VIIB | Clay-224[a] | 1.1:1 | | | F-B | | 30.7 | | 68.9 | |
| | | | 140 | 50 | #1 | 10.9 | 18.3 | 12.9 | 19.7 | 38.1 |
| | | | | | #2 | 11.4 | 19.5 | 12.3 | 20.3 | 36.4 |
| | | | 160 | 50 | #3 | 11.9 | 23.0 | 16.0 | 11.6 | 37.2 |
| | | | | | #4 | 13.3 | 24.2 | 15.0 | 11.1 | 36.2 |
| | | | 160 | 125 | #5 | 11.5 | 20.2 | 19.3 | 17.2 | 31.6 |

[a]Engelhard Clay-224

What is claimed is:

1. In a method for the co-production of methyl tertiary butyl ether plus isobutylene wherein tertiary butanol is reacted with methanol the improvement wherein the tertiary butanol conversion is 80% and the crude product comprises two phases, an isobutylene plus MTBE-rich phase and an aqueous methanol-rich phase, resulting from reacting the tertiary butanol and methanol in a molar ratio of 1:1.1 in one step in a reaction zone in the presence of a montmorillonite clay catalyst consisting of,
an acidic clay of particle size 20/60 mesh, having an acidity of 3.0 mg KOH/gm, a surface area of 350 m$^2$/gm and a moisture content of <1 wt %, at a temperature of 180° C. and a pressure of 300 psig.

* * * * *